United States Patent [19]

Zoeller

[11] Patent Number: 4,914,285

[45] Date of Patent: Apr. 3, 1990

[54] CONTROL MEANS FOR WEB SCANNING APPARATUS

[75] Inventor: Leon R. Zoeller, Hamlin, N.Y.

[73] Assignee: Eastman Kodak Company, Rochester, N.Y.

[21] Appl. No.: 289,873

[22] Filed: Dec. 27, 1988

[51] Int. Cl.$^4$ .............................................. G01J 1/32
[52] U.S. Cl. ................................................ 250/205
[58] Field of Search ............... 250/562, 563, 572, 235, 250/236, 205, 559; 356/237, 429–431; 355/67–69

[56] References Cited

U.S. PATENT DOCUMENTS

| | | | |
|---|---|---|---|
| 4,134,684 | 1/1979 | Jette | 356/430 |
| 4,247,204 | 1/1981 | Merlen et al. | 250/572 |
| 4,711,566 | 12/1987 | Evans | 355/69 |
| 4,814,597 | 3/1989 | Kruger et al. | 250/205 |
| 4,831,247 | 5/1989 | Ishizaka | 350/205 |

Primary Examiner—David C. Nelms
Assistant Examiner—Khaled Shami
Attorney, Agent, or Firm—Armin B. Pagel

[57] ABSTRACT

In an apparatus for scanning a transverse region of moving web, the speed of the web being scanning adjusts the clock of the camera that controls the scanning rate of the camera, to maintain a constant spacing of the scan regions, rather than vice versa, thereby allowing wide variations in web speed while maintaining constant scan region spacing. Additionally, the intensity of the web illumination is controlled as a function of web speed so that each scan region receives the same amount of light from the illumination means during each scan interval regardless of variations in web speed.

4 Claims, 2 Drawing Sheets

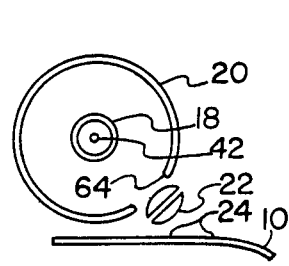
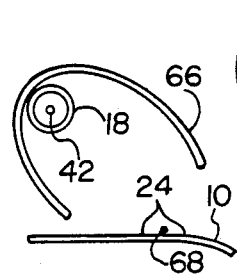
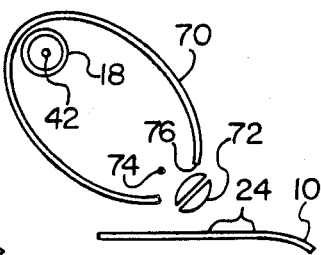
FIG. 3        FIG. 4        FIG. 5
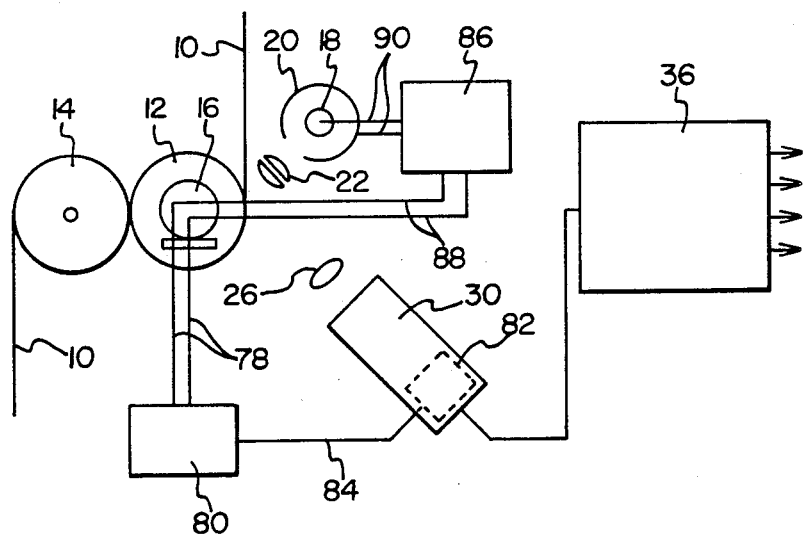
FIG. 6

4,914,285

CONTROL MEANS FOR WEB SCANNING APPARATUS

CROSS REFERENCE TO RELATED APPLICATIONS

Reference is made to commonly owned U.S. Pat. Application No. 289,875 entitled LAMP FOR SCANNING APPARATUS, filed in the name of Jon F. Gehret, and to commonly owned U.S. Pat. Application No. 289,872 entitled WEB SCANNING APPARATUS, filed in the name of Neil A. Hochgraf, both filed concurrently with the present application.

BACKGROUND OF THE INVENTION

1. Field Of The Invention

The present invention relates to optical scanners and more particularly to controlling the scanning rate and illumination intensity in such a scanner as a function of the velocity of a moving web being scanned.

2. Description Relative To The Prior Art

It is well known in the prior art to detect the presence of defects, splices or other irregularities or discontinuities in a moving web by illuminating a transverse region of the web and scanning a region within the illuminated region. Such scanning may be performed by an electronic camera employing either a linear array of photodetectors that view corresponding areas of the illuminated region and that are read out serially, or by means of a single photodetector combined with an optical system that sweeps the viewing area of that detector along the illuminated region.

To detect relatively small or subtle irregularities in a rapidly moving web, the illumination must be of relatively high intensity. For example, U.S. Pat. No. 4,752,897, issued on June 21, 1988 in the names of Leon Zoeller et al. discloses such an apparatus capable of scanning a web at extremely high speeds, requiring handling of the resulting digital signals at data rates of the order of tens of megabytes per second. This requires quite brilliant illumination because of the extremely short duration during which each individual area of the web or the like is accessed. Correlatively, the illumination must be uniform across the width of the web so that variations in the intensity of the light received by the photodetector are attributable to variations in the web and not to variations in its illumination. In accordance with the invention disclosed in the above-identified commonly owned U.S. Pat. Applications, Ser. Nos. 289,875 and 289,872, the latter requirement is achieved by illumination means comprising a single elongate incandescent filament supported only by its ends.

The foregoing Zoeller et al. U.S. Pat. also discloses the concept of maintaining equal spacing of the scan regions by using the clock signals that control the scanner to adjust the web speed so that the web moves past the scanner at the exact speed required to achieve that equality, but does not provide means for maintaining the equality of the scan region spacing if the speed of the web varies significantly, as is often dictated by other operations being performed on the web. Also, no means are disclosed for controlling illumination of the web scanning region as a function of web speed so that such speed changes do not influence the output of the camera.

SUMMARY OF THE INVENTION

In accordance with the present invention, the speed of the web being scanned adjusts the clock that controls the scanning rate of the camera to maintain a constant spacing of the scan regions, rather than vice versa, thereby allowing wide variations in web speed while maintaining constant scan region spacing. Additionally, the intensity of the web illumination is controlled as a function of web speed so that each scan region receives the same amount of light from the illumination means during each scan interval, regardless of variations in web speed.

Various means for practicing the invention and other advantages and novel features thereof will be apparent from the following description of illustrative embodiments of the invention, reference being made to the accompanying drawings.

BRIEF DESCRIPTION OF THE DRAWINGS

FIG. 3 illustrates means for focusing illumination from the elongate incandescent lamp onto the web to illuminate a transverse region thereof, employing an elongate reflector of circular cross section in combination with cylindrical lens means;

FIG. 4 depicts an alternative focusing arrangement employing a reflector of elliptical cross section;

FIG. 5 depicts another alternative focusing arrangement employing a reflector of elliptical in combination with cylindrical lens means; and FIG. 6 is a block diagram of a system according to the invention for controlling the scanning rate and illumination intensity of the illustrative apparatus as a function of web speed.

DESCRIPTION OF THE ILLUSTRATIVE PREFERRED EMBODIMENTS

Figure 1:
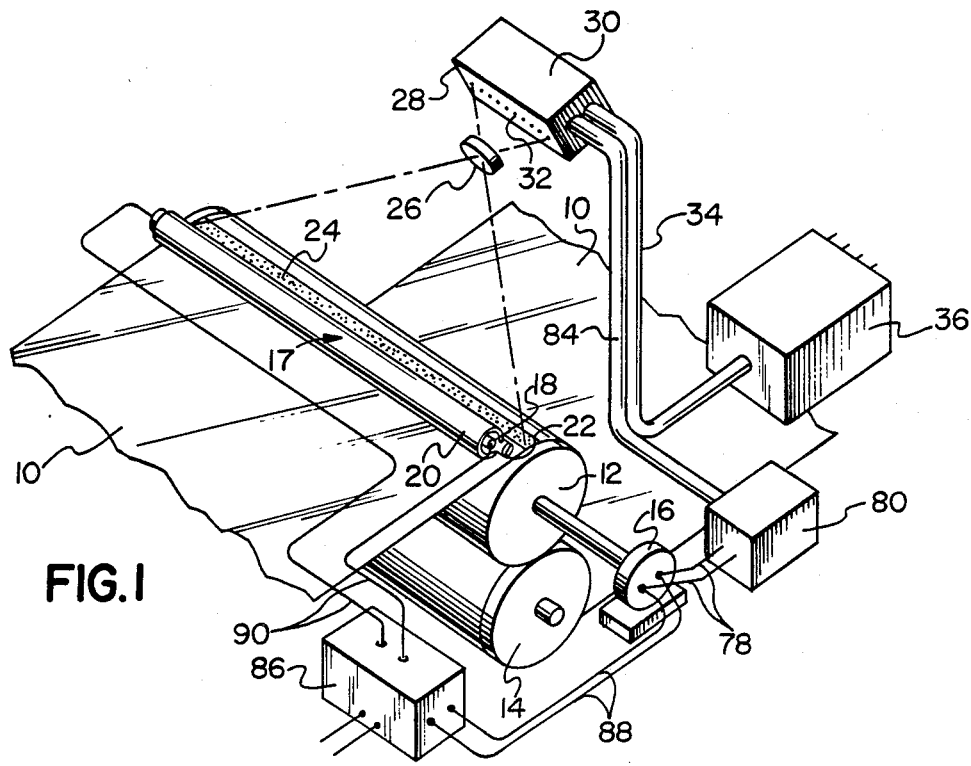
FIG. 1 is a schematic perspective illustration of a web defect scanning apparatus according to a preferred illustrative embodiment of the invention.

In FIG. 1 a web 10 is shown being moved longitudinally while wrapped partially around rollers 12 and 14. One of these two rollers might serve to drive the web, but in any event the surface velocity of either roller is the same as that of the confronting surface of the web so that the linear velocity of the web can be monitored, for example by a tachometer sensing device 16 or by an analogous device such as a tachometer driven by an idler wheel pressed against the web.

An illumination device 17 comprises an elongate incandescent lamp 18 provided with an internally reflective reflector 20 in the form of a slotted cylinder of circular cross section and an elongate cylindrical lens assembly 22. The illumination device 17 is supported adjacent the web 10 in parallel relation thereto so that the lamp illuminates a transverse region 24 of the web, as described below with reference to FIGS. 4, 5 and 6. A scanning region of the illuminated region 24, in turn, is imaged by a conventional lens 26 onto detector face 28 of a linear CCD (charge couple device) camera 30, which includes a row of small and closely spaced individual detector sites represented as dots along dotted line 32. Accordingly, each individual detector site views a corresponding area along the transverse illumination region 24. The camera also includes a clock that controls clocking of the successive signals out of the camera and a signal transmitter that changes the level of the signal and transforms it into a signal that has more noise immunity for transmission, for example via a coaxial cable 34, by which the camera is connected to a receiver device within parallel processing computer 36. As described in the previously identified U.S. Pat. Zoeller et al., the signals emanating from the camera and fed to the computer 36 are digitized to provide a continuous flow of first digital signals and the computer 36 includes means which are operative continuously and in parallel upon the first digital signals for reducing the first digital signals into a continuous flow of second digital signals occurring at a reduced rate from the rate of flow of the first digital signals. These second digital signals represent predetermined events in the process, such as critical parameters and defects in a web. Finally, means are also provided in the computer 36 which are responsive to and operative continuously upon the second digital signals for providing outputs representing the analysis of certain effects in the process represented by the events, for example outputs representing statistical quality control information as to the categories, location and even the source of the events (e.g., the defects or imperfections in the web).

Figure 2:
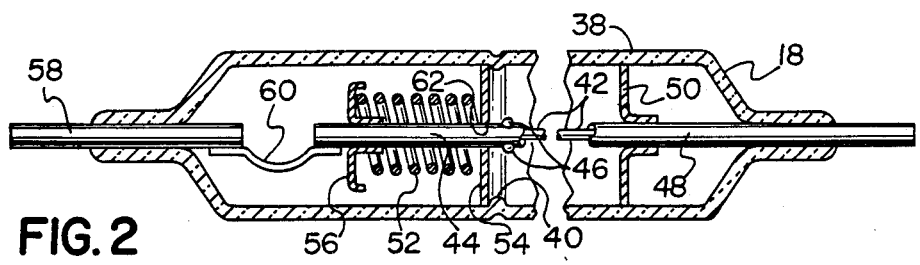
FIG. 2 is a fragmentary elevational view of the elongate incandescent lamp employed in the apparatus depicted in FIG. 1.

The elongate incandescent lamp 18, best depicted in FIG. 2, comprises a long straight cylindrical tube 38 made of transparent glass or quartz and provided near one end with abutment means comprising an internal annular ridge 40 or a corresponding structure comprising annularly disposed internal bumps. The filament assembly, which is fabricated before being installed in the tube, comprises an elongate filament 42 made of tungsten, platinum, nichrome or some other appropriate metal or metal alloy.

At one end, the filament is swaged into a tubular conductive metal support rod 44 provided with three equiangularly disposed protrusions, two of which are shown at numeral 46. At its other end the filament is swaged into a similar longer tubular support and terminal rod 48, which is provided with an annular metal flange 50 of a diameter appropriate to fit slidably within the bore of tube 38. A compression spring 52 surrounds filament support rod 44 and is seated against a support washer 54 that slidably supports rod 44 and which is of a diameter appropriate to allow the washer to slide within the bore of tube 38 and to seat against internal annular ridge 40. At its other end, spring 52 is seated against metal spring engaging member 56, which is swaged or welded to support rod 44. Before the filament assembly is installed in tube 38, washer 54 is seated against protrusions 46 by spring 52, which is compressed somewhat between washer 54 and member 56. At its outer end, beyond member 56, support rod 44 is electrically connected to a terminal rod 58 by a flexible metallic conductor strap 60.

To assemble the lamp, the support and terminal rod 48 is fed through the bore of tube 18, which at that stage is open at both ends, and the tube is heated and closed around terminal rod 58 to hermetically seal that end of the lamp tube with rod 58 located substantially coaxial with tube 38. As is well known in the art, rods 58 and 48 are preferably made of an alloy having substantially the same coefficient of thermal expansion as that of the transparent lamp tube to allow direct hermetic sealing between those materials, but other known techniques can also be employed to accomplish such sealing, e.g. a soldering technique. After terminal rod 58 is sealed into the tube, sufficient tension is applied to support and terminal rod 48 to further compress spring 52 and thereby move protrusions 46 away from washer 54, which is seated against annular ridge 40. While terminal rod 48 is held in this position, centered in tube 38 by flange 50, the tube is evacuated and the end of the tube surrounding rod 48 is heated so that it can be closed around rod 48 in hermetically sealed relation thereto; whereupon the tube is allowed to cool and the tension on rod 48 is then released to complete the assembly procedure.

When the lamp is energized, the filament elongates because of its thermal expansion but is maintained constantly under tension and thereby prevented from sagging by spring 52 as support rod 44 slides within central hole 62 of washer 54. Because the filament supporting ends of the support rods 44 and 48 are maintained in coaxial relation to tube 38 by washer 54 and flange 50, respectively, thermal distortion of these support rods or of spring 52 does not effect the location of the filament in relation to the tube, and because the compression spring does not support the filament directly, the location of the filament is not dependent on the dimensional accuracy of the spring itself. It should be noted that spring 52 conducts, at most, only a very small portion of the filament current, or no current at all if washer 54 is made of a non-conductive material, e.g. a ceramic material. Also, because of the high conductivity of rod 44 compared to filament 42, relatively little heat is radiated by rod 44 to spring 52, which is shielded from direct radiation from filament 42 by washer 54. By virtue of these features, the filament is initially coaxial with tube 38 and remains so during the operation of the lamp and is supported only by its ends, without the need for auxiliary support means along the length of the filament.

To illuminate the narrow transverse region 24 of the moving web, the lamp 18 is shown in FIG. 3 partially surrounded by a concentric cylindrical reflector 20 of circular cross section provided with an elongate slot 64. This form of reflector reflects back to the filament most of the radiation striking the reflector and thereby improves the efficiency of the lamp by contributing to maintaining the filament at its required temperature. The filament itself is imaged to illuminate the transverse web region 24 by an elongate cylindrical converging lens assembly 22, which is depicted as comprising two plano-concave elements. Instead of comprising a separate element, the cylindrical reflector could comprise a reflective coating provided directly on the outer cylindrical surface of tube 38 except along an elongate region corresponding to slot 64. Alternatively, FIG. 4 shows the lamp partially surrounded by an elongate reflector 66 of elliptical cross section with the lamp filament 42 located along one focal axis of the reflector and with the web located at or near the other focal axis 68; each such axis being defined by the corresponding focal points of the cross sections of the elliptical reflector. Accordingly, the light striking the reflector is focused onto the web area 24. FIG. 5 shows another embodiment in which an elliptical reflector 70 partially surrounds the lamp, with the lamp filament 42 located along the first focal axis and with a cylindrical lens assembly 72 located beyond the second focal axis 74 along slot 76 so that most of the light reaching the lens is converged into the web area 24 and most of the remaining light is reflected back to the filament to help maintain its desired temperature.

In the apparatus disclosed in the foregoing Zoeller et al. U.S. Pat., the web is run at a nominal rate and the clock means employed to clock the successive analog signal out of the camera also serves to lock a phase-lock loop that produces synchronizing signals at the line rate. These line-rate signals are transmitted to the web encoder interface and may be used to make adjustments to the nominal speed to maintain equal spacing of the scan regions, i.e. the successive regions scanned by the camera, which are narrower than the illumination area 24.

In many applications, the speed of a web being inspected is not constant, but changes over a wide range because of the operations being performed on the web. Although it would be possible to modify the above described apparatus to maintain the scan regions equally spaced under such circumstances, e.g. changing the scanner clock rate and thereby controlling the web-drive device over a wide range of speeds, this approach is undesirable because of the mechanical inertia in the drive system and the difficulty in achieving accurate speed control of the drive means. In accordance with the present invention, however, the arrangement shown in FIGS. 1 and 6 employs tachometer 16 to measure the web velocity, as established by the drive motor and other influences, and to control the scanning rate accordingly, so that the scan regions are equally spaced to provide the same amount of information from the camera as the web moves a predetermined distance, regardless of the web speed. As shown in FIGS. 1 and 6, this is accomplished by feeding velocity output signals from tahcometer 16 through wires 78 to synchronizing unit 80, which converts the tachometer output signal to a form and frequency range compatible with the signals from scanning clock 82 (FIG. 6) within camera 30. The synchronizing unit is connected to the camera clock 82 by cable 84 and controls the clocking rate of that clock as a function of the web speed, for example, by means of a phase lock loop within the synchronizing unit that changes the clock rate to keep the clock signals in synchronism with the converted tachometer signals. Consequently, rather than having the clock rate determine the web velocity, the web-velocity determines the clock rate so that the scan regions are equally spaced. The resulting camera output signal is fed to a signal transmitter included in the camera, as explained in the Zoeller et al. patent in connection with FIG. 3, thereof, and is then transmitted to a receiver in computer 36 and further processed as taught by that patent.

If the web speed is adjusted only slightly from a nominal speed, as proposed in the Zoeller et al. patent discussed above, the variation in the amount of illumination received by each detector site of the camera during each scan of web areas of equal reflectance is proportionally small and can probably be disregarded. However, if the web speed is changed significantly while maintaining constant scan region spacing, this difference becomes proportionately significant. For example, if the web slows down, each scan region is illuminated for a longer time during each scan interval and, because the detectors integrate the total amount of light received during each scanning cycle, the resulting increased output of the detectors cannot be distinguished from increased output attributable to increased reflectivity of the web. Also, the camera and its associated circuitry are typically designed for maximum sensitivity within a particular luminance range. Accordingly, tachometer 16 also provides web speed signals to illumination control device 86 through wires 88, whereby device 86 adjusts the current flow to lamp 18 through wires 90 so that the total amount of light received by the camera detectors during each scan cycle of a web of constant reflectivity is likewise substantially constant, regardless of the velocity of the web. A microprocessor or the like may be incorporated in or associated with illumination control device 86 to adjust the energization of the lamp, not only as a function of web speed but also as a previously determined function of the spectral characteristics of the lamp itself under different energization conditions. For example, if the camera is selectively sensitive to light toward the red end of the spectrum, an increase in voltage to the lamp required by a higher web speed takes into account the shift of the lamp spectrum toward the violet range as its filament temperature increases, which can be represented by an appropriate algorithm or look up table in the microprocessor.

The invention has been described with reference to illustrative preferred embodiments but variations and modifications are possible within the spirit and scope of the invention as defined by the following claims.

I Claim:

1. In an apparatus for scanning a transverse region of a moving web, said apparatus comprising:
    (a) driving means for moving said web along a predetermined path;
    (b) scanning means for scanning successive transverse scanning regions of said web during respective successive scanning intervals as said web is moved past said scanning means by said drive means; and
    (c) illumination means for illuminating the illumination region of said web scanned by said scanning means, the improvement means comprising;
    (d) sensing means for sensing the speed at which said moving web moves past said scanning means; and
    (e) illumination intensity control means for adjusting the intensity of the illumination provided by said illumination means as a function of the web speed sensed by said sensing means so that each scanned web region receives the same amount of light from said illumination means during each scan interval regardless of web speed.

2. The invention defined by claim 1 in which said illumination means comprises an elongate incandescent lamp and in which said illumination control means adjusts the intensity of the illumination provided thereby by adjusting the current flowing through side lamp.

3. In an apparatus for scanning a transverse region of a moving web, said apparatus comprising:
    (a) driving means for moving said web along a predetermined path;
    (b) scanning means for scanning successive scanning regions of said web transverse to said web and said path as said web is moved past said scanning means by said driving means, said scanning means including clock means for controlling the scanning rate of said scanning means, the improvement comprising;
    (c) sensing means for sensing the speed at which said moving web moves past said scanning means; and
    (d) scanning rate control means for adjusting said clock means as a function of the web speed sensed by said sensing means so that successive scanning regions are equally spaced along said web.

4. In an apparatus for scanning a transverse region of a moving web, said apparatus comprising:

(a) driving means for moving said web along a predetermined path;
(b) scanning means for scanning successive transverse scanning regions of said web during respective successive scanning intervals as said web is moved past said scanning means by said drive means; and
(c) illumination means for illuminating the region of said web scanned by said scanning means, the improvement comprising;
(d) sensing means for sensing the speed at which said moving web moves past said scanning means;
(e) illumination intensity control means for adjusting the intensity of the illumination provided by said illumination means as a function of the web speed sensed by said sensing means so that each scanned web region receives the same amount of light from said illumination means during each scan interval regardless of web speed; and
(f) scanning rate control means for adjusting said clock means as a function of the web speed sensed by said sensing means so that successive scanning regions are equally spaced along said web.

* * * * *